United States Patent
Bijloo et al.

(10) Patent No.: US 10,383,989 B2
(45) Date of Patent: Aug. 20, 2019

(54) BREAST PUMP SYSTEM

(71) Applicant: KONINKLIJKE PHILIPS N.V., Eindhoven (NL)

(72) Inventors: Michiel Dirk Augustinus Bijloo, Eindhoven (NL); Rachel Estelle Thilwind, Eindhoven (NL); Leonardus Maria Poppelier, Eindhoven (NL); Arnold Aalders, Eindhoven (NL)

(73) Assignee: KONINKLIJKE PHILIPS N.V., Eindhoven ( * ) Notice: Subject to any disclaimer, the term of this patent is extended or adjusted under 35 U.S.C. 154(b) by 449 days.

(21) Appl. No.: 14/430,347

(22) PCT Filed: Sep. 23, 2013

(86) PCT No.: PCT/EP2013/069758
§ 371 (c)(1),
(2) Date: Mar. 23, 2015

(87) PCT Pub. No.: WO2014/044858
PCT Pub. Date: Mar. 27, 2014

(65) Prior Publication Data
US 2015/0238670 A1 Aug. 27, 2015

Related U.S. Application Data

(60) Provisional application No. 61/704,729, filed on Sep. 24, 2012.

(30) Foreign Application Priority Data

Sep. 24, 2012 (EP) .................................... 12185597

(51) Int. Cl.
*A61M 1/06* (2006.01)
*A61M 5/14* (2006.01)

(52) U.S. Cl.
CPC .............. *A61M 1/06* (2013.01); *A61M 1/062* (2014.02); *A61M 5/1418* (2013.01); *A61M 2209/08* (2013.01)

(58) Field of Classification Search
CPC ............ A61M 1/06; A61M 2039/0081; A61M 2209/08; A61M 2005/14268; A61M 2005/1587; A61M 5/14248; A61M 5/1418
See application file for complete search history.

(56) References Cited

U.S. PATENT DOCUMENTS 5,071,403 A * 12/1991 Larsson .................. A61M 1/06
604/320
5,094,591 A * 3/1992 Whitley, II ........... F04D 29/426
417/234

(Continued)

FOREIGN PATENT DOCUMENTS

CN 101959547 A 1/2011
JP 2000093524 A 4/2000

(Continued)

OTHER PUBLICATIONS onebabyworld.com/nusing-breastfeeding-breastpumps-c-4_17.html?; Jun. 16, 2011, 1 page.*

*Primary Examiner* — Nathan R Price
*Assistant Examiner* — Justin L Zamory (57) ABSTRACT

The present application relates to an operating unit for a breast pump system. The operating unit comprises a housing and a vacuum pump received in said housing. The housing has a connector (15) for attaching a tube and an outer surface (11) about which a tube can be wrapped. At least a section of the outer surface (11) is curved so that the tube can be wrapped about the housing without buckling. The outer surface (11) comprises a recess (14) and the connector (15) is located in the recess (14), wherein a surface of the recess (14) distends away from the connector (15) so that when a (Continued)

tube is attached to the connector (15), a portion of the tube proximal to the connector (15) does not buckle.

14 Claims, 5 Drawing Sheets

(56) References Cited

U.S. PATENT DOCUMENTS

| | | | |
|---|---|---|---|
| 5,520,643 A * | 5/1996 | Ensminger | A61M 39/0208 |
| | | | 604/175 |
| 5,720,722 A | 2/1998 | Lockridge | |
| 5,807,335 A * | 9/1998 | Kriesel | A61M 5/152 |
| | | | 604/131 |
| 6,004,186 A | 12/1999 | Penny | |
| 6,547,756 B1 | 4/2003 | Greter | |
| 2001/0038799 A1 | 11/2001 | Silver | |
| 2001/0047148 A1 | 11/2001 | Suh | |
| 2004/0087898 A1 | 5/2004 | Weniger | |
| 2007/0093762 A1 * | 4/2007 | Utterberg | A61M 39/02 |
| | | | 604/256 |
| 2007/0135761 A1 | 6/2007 | Cheng | |
| 2008/0011907 A1 | 1/2008 | Jacobsma | |
| 2008/0090445 A1 | 4/2008 | Luzbetak | |
| 2008/0146999 A1 | 6/2008 | Tanaka | |
| 2009/0281497 A1 * | 11/2009 | Kamen | A61M 5/1413 |
| | | | 604/151 |
| 2010/0019107 A1 * | 1/2010 | McCloud | A61M 16/0875 |
| | | | 248/83 |
| 2011/0098639 A1 | 4/2011 | Kirchner | |

FOREIGN PATENT DOCUMENTS

| | | |
|---|---|---|
| JP | 2009192002 A | 8/2009 |
| WO | 2004009151 A1 | 1/2004 |
| WO | 2007061644 A2 | 5/2007 |
| WO | 2009088956 A2 | 7/2009 |
| WO | 2010083485 A2 | 7/2010 |

* cited by examiner

BREAST PUMP SYSTEM

This application is the U.S. National Phase application under 35 U.S.C. § 371 of International Application No. PCT/EP2013/069758, filed on Sep. 23, 2013, which claims the benefit of U.S. Provisional Application No. 61/704,729 filed on Sep. 24, 2012 and European Application No. 12185597.7 filed Sep. 24, 2012. These applications are hereby incorporated by reference herein.

FIELD OF THE INVENTION

The present invention relates to a breast pump system, in particular to an operating unit for operating a breast pump.

BACKGROUND OF THE INVENTION

A breast pump system comprises a breast pump acting as an expression unit, and an operating unit to operate the breast pump. The expression unit has a funnel which receives the breast and a receptacle in which the expressed milk is collected. The operating unit comprises a vacuum pump driven by a motor. In use, the vacuum pump applies a vacuum to the breast which enables milk to be expressed. The vacuum is applied to the breast either directly or via a membrane located in the expression unit which deforms and so causes a vacuum to be generated in the funnel.

Breast pump systems are typically configured to be assembled and disassembled so that any part of the breast pump system that has been in contact with breast milk can be sterilised after each use and so that the breast pump system can be stored in a convenient place when it is not being used. However, when storing a breast pump system in a disassembled state, there is a risk of damaging or losing parts of the breast pump system.

SUMMARY OF THE INVENTION

It is an object of the invention to provide an operating unit and a breast pump system which substantially alleviates or overcomes the problems mentioned above.

According to the present invention, there is provided an operating unit for a breast pump system, comprising a housing and a vacuum pump received in said housing, the housing having a connector for attaching a tube, and an outer surface about which a tube can be wrapped, wherein at least a section of the outer surface is curved so that the tube can be wrapped about the housing without buckling, wherein the outer surface comprises a recess and the connector is located in the recess, and wherein a surface of the recess distends away from the connector so that when a tube is attached to the connector, a portion of the tube proximal to the connector does not buckle.

This provides the advantage that when the breast pump system is not in use, the operating unit can easily be put away, stored or transported as the tube can be neatly wrapped around the housing. By wrapping the tube around the housing, the risk of losing the tube is minimised. Furthermore, the curved section of the outer surface of the housing prevents the tube from buckling which can damage the tube. Buckling is to be understood as including collapsing, kinking or folding of the tube.

It is noted that an operating unit for a breast pump system in which at least a section of an outer surface of a housing is curved is known per se, for example, from U.S. Pat. No. 6,547,756 B1, WO 2010083485 A2 and DE 10 2004 030 692 B3.

The present invention further provides the advantage that the surface of the recess that distends away from the connector guides and supports the tube in any direction away from the housing such that it prevents the tube from buckling or kinking during use and when stored. Furthermore, it enables the tube to be wrapped around the housing in any direction. Additionally, the user can be located in any direction relative to the housing as long as they are within the length of the tube.

In one embodiment, at least the section of the outer surface that is curved may comprise a plurality of linear sections that extend at an oblique angle to each other.

This provides the advantage that as the tube is wrapped around the housing, the curved section of the outer surface that comprises the plurality of linear sections prevents the tube from buckling which can damage the tube.

In an alternative embodiment, at least the section of the outer surface that is curved may comprise a radius.

This provides the advantage that this curved section of the outer surface of the housing prevents the tube from buckling which can damage the tube.

In another embodiment, the outer surface may further comprise a straight section.

This provides the advantage that the curved section and the straight section both support the tube as it is wrapped around the housing.

In one embodiment, the outer surface may be continuously curved.

This provides the advantage that the tube may be continuously supported as the tube is wrapped around the housing.

In another embodiment, the outer surface has a lip so to retain a tube wrapped around the housing.

This provides the advantage that when a tube is wrapped around the housing, the lip helps preventing the tube from sliding off the housing.

Preferably, the outer surface is formed with at least one ridge for guiding the tube around the housing.

This provides the advantage that the ridge guides the tube around the housing so that it is neatly wrapped around the housing. Furthermore, the ridge supports the tube such that it helps preventing the tube from sliding off the housing.

Preferably, the connector comprises a hollow pin extending from the recess such that a tube can be attached to the pin by inserting the pin into the tube.

This provides the advantage that the tube is removably attached to the housing and that the tube is in fluid communication with the vacuum pump.

Preferably, the hollow pin is integrally formed with the surface of the recess.

This provides the advantage that the housing is easy to assemble and easier to keep clean.

In one embodiment, the outer surface of the housing may be a continuous peripheral outer surface.

This provides the advantage that when a tube is wrapped around the housing, it is continuously supported by the outer surface such that it does not have areas of concentrated stress.

In one embodiment, the outer surface may be circumferentially curved.

According to another aspect of the invention, there is provided a breast pump system comprising an operating unit as described above and a tube, the tube having a first end attachable to the connector and a second end, and the breast pump system further comprises an attachment member configured to secure the second end of tube when the tube is wrapped around the housing.

This provides the advantage that when the tube is wrapped around the housing it can be secured in its wrapped position such that the operating unit and the tube can easily be packed away, stored or transported. Furthermore, there are no loosely hanging parts which may otherwise be damaged. Additionally, when the tube is wrapped around the housing, it is signalled to the user that it can easily be unwound and used immediately.

In one embodiment, the attachment member may be configured to attach the second end of the tube to another part of the tube.

In another embodiment, the attachment member may be configured to attach the second end of the tube to the housing.

In one embodiment, the attachment member may be integrally formed with the housing.

This provides the advantage that the tube can be secured in a wrapped position around the housing and that the attachment member cannot be accidentally lost.

Preferably, the attachment member comprises a cap configured to be removably attachable to a main body of an expression unit.

This provides the advantage that also the cap can be safely stored or transported.

Conveniently, the cap may be attachable to the second end of the tube and the cap may comprise a clip so that the second end of the tube is attachable to another part of the tube.

The cap and the tube are generally not in contact with expressed milk and so do not need to be disassembled and sterilised unlike other parts of the breast pump system that are in contact with expressed milk. In the embodiment where the attachment member comprises a cap and a clip, and the attachment member is used for securing the tube in a wrapped position, it provides the advantage that the risk of accidentally losing the cap when the breast pump is stored is minimised.

Preferably, the clip is integrally formed with the cap.

This provides the advantage that the clip cannot disconnect from the cap which could cause the tube to unwound from the housing.

In one embodiment, the attachment member may be configured to attach the first end of the tube with the second end of the tube as the tube is wrapped around the housing.

This provides the advantage that an end of the tube does not have to be attached to the housing in order to secure the tube wrapped around the housing.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF THE EMBODIMENTS

Figure 1:
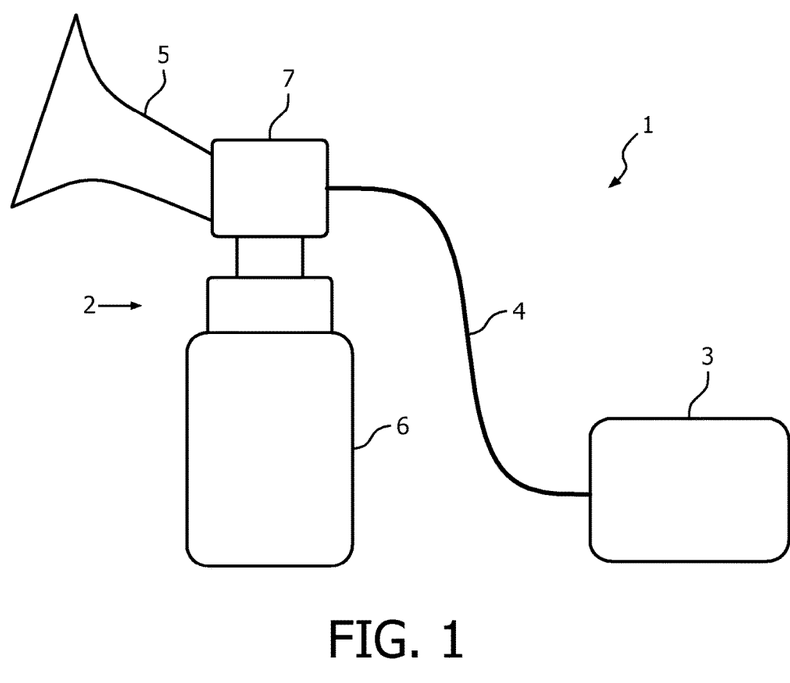
FIG. 1 shows a breast pump system according to an embodiment of the present invention.

Referring now to the drawings, a breast pump system according to an embodiment is shown in FIG. 1. The breast pump system 1 comprises an expression unit 2 and an operating unit 3 which are connected via a tube 4.

The expression unit 2 is formed with a main body 7, a funnel 5 for receiving a breast of a user and a receptacle 6 for collecting the expressed milk. The funnel 5 and the receptacle 6 are connected to the main body 7. The main body 7 comprises a vacuum chamber (not shown). A flexible membrane or diaphragm (not shown) is located in the vacuum chamber.

The operating unit 3 comprises a controller (not shown), a power source (not shown), a motor (not shown) and a vacuum pump (not shown). The controller controls the operation of the power source, motor and vacuum pump. In use, the vacuum pump applies a vacuum to the membrane located in the main body 7 so that it deforms. The flexible membrane deforms to create a vacuum in the funnel 5 which in turns applies a vacuum to the breast which enables milk to be expressed. The membrane also prevents expressed milk from flowing into the tube 4 leading to the operating unit 3. In one embodiment, the membrane inverts as the membrane deforms. However, in an alternative embodiment the membrane does not invert.

Although the breast pump system is described as comprising a membrane such that the vacuum is applied indirectly to the breast, it should be understood that in an alternative embodiment, the vacuum is applied directly to the breast of a user. In this embodiment, the breast pump system does not comprise a membrane and the vacuum created by the vacuum pump is applied directly to the breast.

Figure 2:
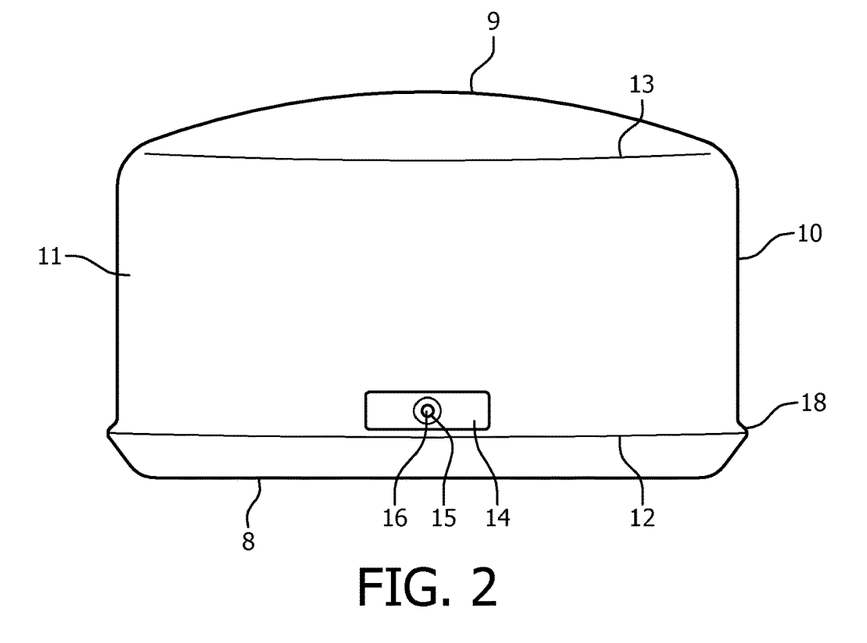
FIG. 2 shows an operating unit according to an embodiment of the present invention.

Referring now to FIG. 2, the operating unit 3 comprises a housing having a base wall 8, a top wall 9, and a side wall 10 extending between the base wall 8 and the top wall 9. The base wall 8, top wall 9 and side wall 10 define a space for holding at least the controller, vacuum unit or vacuum pump, and power source. The base wall 8, top wall 9 and side wall 10 can be integrally formed or manufactured separately and thereafter assembled into the housing.

The top wall 9 and the base wall 8 can be of any shape.

Figure 3:
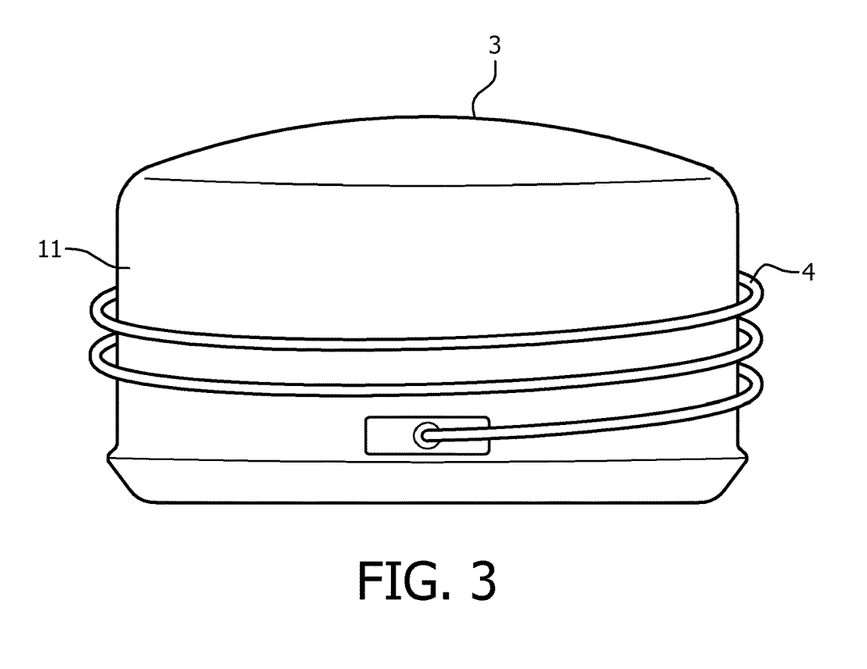
FIG. 3 shows the operating unit in FIG. 2 with a tube wrapped around a housing of the operating unit.

The side wall 10 of the housing has an outer surface 11 that is continuously curved such that the periphery of the housing forms an ellipse. The curved outer surface enables the tube 4 to be wrapped around the housing of the operating unit 3 without the tube 4 buckling. Thus, when the breast pump system 1 has been used and is dissembled to be put away, the tube 4 can be wrapped around the outer surface of the side wall 10 of the housing. The tube 4 wrapped around the housing is shown in FIG. 3.

Although the outer surface 11 has been described above as being continuously or circumferentially curved it is intended that the scope of the present invention also includes an outer surface of a side wall of a housing wherein only a section is curved. For example, the outer surface may also comprise a straight section. In one embodiment, the outer surface comprises two curved sections and two straight sections of the outer surface such that the periphery of the housing is oblong or obround. It shall also be understood that the outer surface may alternatively be shaped so that the periphery of the housing is round, oval or egg-shaped, or yet in an alternative embodiment, the outer surface is shaped such that the housing is square but wherein the corners are curved or rounded.

It shall be appreciated that the curved section of the outer surface 11 of the side wall in any of the above mentioned embodiments is a chamfer. Furthermore, the curved section of the outer surface in any of the above mentioned embodiments may comprise a radius such that it is circumferentially curved. It is also envisaged that the curved section of the above mentioned embodiments may alternatively comprise a plurality of linear sections that extend at an oblique angle to each other. In this embodiment, the plurality of linear sections are connected to each other at an angle such that when a tube is wrapped around the housing, the curved section comprising said plurality of linear sections, prevents the tube from buckling or kinking.

The outer surface comprises a first edge 12 which meets the base wall 8 and a second edge 13 which meets the top wall 9 as seen in FIG. 2. The first and the second edges 12, 13 are parallel, however this is optional. Furthermore, the first and second edges 12, 13 are parallel to the direction in which the tube 4 is wrapped around the housing, however it should be appreciated that also this is optional.

Figure 4:
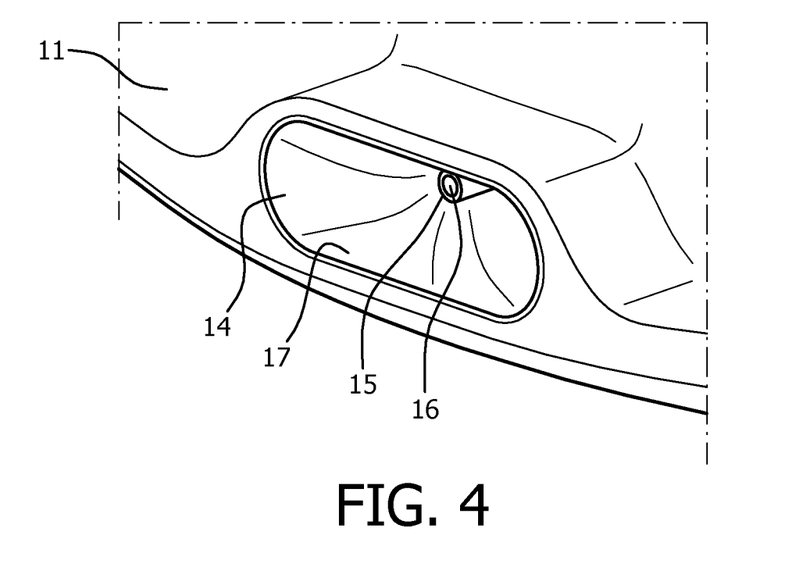
FIG. 4 shows a connector, and a recess of the operating unit.
Figure 6:
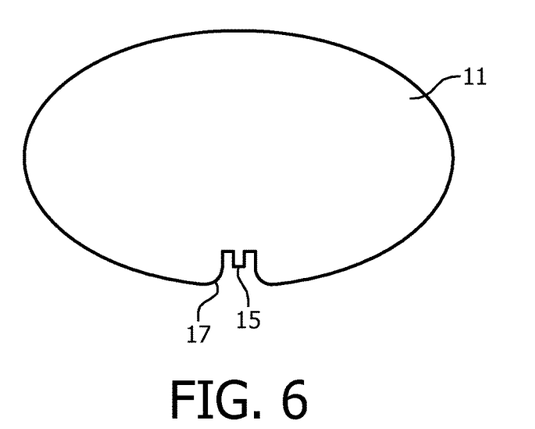
FIG. 6 shows an illustration of a cross-section of the operating unit shown in FIGS. 2 to 4.

Adjacent to the first edge 12, the outer surface is formed with a recess 14 wherein a connector 15 is located. As best seen in FIGS. 4 and 6, the connector 15 is a hollow pin 16 that extends through the recess 14 such that the tube 4 can be connected to the pin 16 by inserting the pin 16 into an opened end of the tube 4. In an alternative embodiment, the connector is a passage or a hole in the housing through which an end of the tube can be inserted. The function of the connector 15 is to attach the tube 4 to the housing so that it is in gaseous or fluid communication with the vacuum pump.

Figure 5:
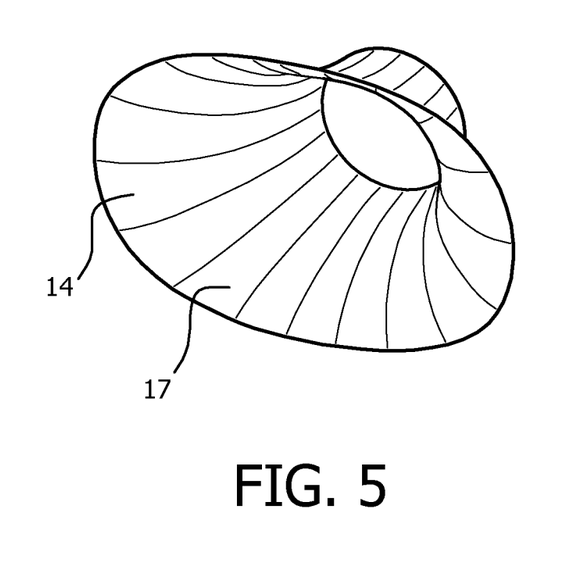
FIG. 5 shows an illustration of the shape of a surface of the recess according to one embodiment.

The recess 14 has a surface 17 that distends or curves away from the connector 15 such that the surface 17 of the recess 14 is formed as a trumpet or a partial toroid as is illustrated in FIG. 5. The surface 17 of the recess curves away from the connector 15 or pin 16 in all directions. The curvature of the surface 17 may be the same in all directions, or alternatively the curvature of the surface 17 may differ between directions. The advantage of the surface 17 of the recess 14 distending or curving away from the connector 15 is that it guides and supports the tube 4 when it is connected to the connector 15 such that the portion of the tube 4 proximal to the connector 15 does not buckle or kink during use or when stored. The radius of the curvature of the surface 17 required so that the tube 4 does not buckle or kink depends on the flexibility and dimensions of the tube 4.

The recess 14 and the connector 15 are located adjacent to the first edge 12 as seen in FIG. 2. This enables the tube 4 to be wrapped around a larger surface area of the outer surface 11 than if the recess 14 and the connector 15 were located equidistant from the first and second edges. However, it shall be understood that the present invention is not limited to the recess 14 and the connector 15 being located adjacent to the first edge 12. In an alternative embodiment, the recess 14 and the connector 15 are located adjacent to the second edge, and yet in another alternative embodiment the recess 14 and the connector 15 are located at a distance between the first and the second edge 12, 13.

The outer surface is further formed with a lip or shoulder 18 as is best seen in FIG. 2. The lip is adjacent to the first edge 12, however it shall be appreciated that the lip 18 may alternatively be adjacent to the second edge 13 or at a distance between 12 and 13. In another alternative embodiment, a first lip is formed adjacent to the first edge 12 and a second lip is formed adjacent to the second edge 13. The lip 18 or lips help the tube 4 to be retained on the housing when it has been wrapped around the housing. Thus, the lip or lips prevent the tube 4 from sliding off the housing when it is wrapped around the housing.

The outer surface 11 of the housing may be formed with a ridge or a plurality of ridges that extend parallel to the direction in which the tube 4 is wound around the housing. The ridge or ridges guides the tube 4 around the housing. Furthermore, the ridge or ridges supports the tube 4 such that it helps preventing the tube from sliding off the housing.

Figure 7:
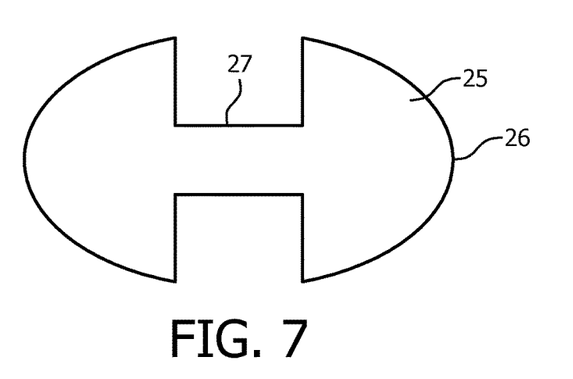
FIG. 7 shows an illustration of a cross-section of an operating unit according to another embodiment.

In an alternative embodiment as is illustrated in FIG. 7, the housing of the operating unit 25 comprises an outer surface 26 that is not continuously in contact with the tube 4 when the tube is wrapped around the housing. In this embodiment, the outer surface 26 has a central portion 27 that extends towards the centre of the operating unit 25 that is not in contact with the tube when the tube is wrapped around the housing.

Figure 8:
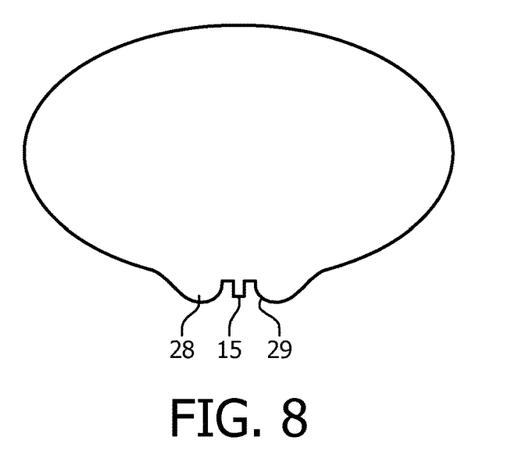
FIG. 8 shows an illustration of a cross-section of an operating unit according to yet another embodiment.

In yet another alternative embodiment as illustrated in FIG. 8, the connector 15 is located in a recess that is formed by an annular protrusion 28. The recess has a surface 29 that distends or curves away from the connector 15 similar to the embodiment described with reference to FIG. 6, and so also the surface 29 of the recess of this embodiment guides and supports the tube when it is connected to the connector such that the portion of the tube proximal to the connector 15 does not buckle or kink during use and storage. The connector 15 may be a pin as illustrated in FIG. 8 or it may be an opening or a hole through which the tube is inserted.

The breast pump system 1 according to any of the embodiments described above may further comprise an attachment member for securing the tube 4 in its wrapped position around the housing or for securing an end of the tube to the main body 7 as is described below. The attachment member may either directly or indirectly secure the tube in its wrapped position or to the main body 7.

Figure 10:
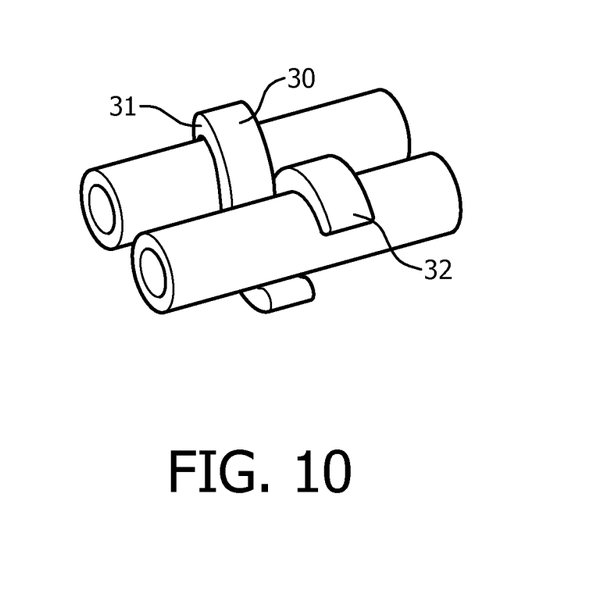
FIG. 10 shows an embodiment of an attachment member according to another embodiment.

In one embodiment of the breast pump system, a first end of the tube 4 is attached to the connector 15 as described above. This provides an anchoring point for the tube 4 as it is being wrapped around the housing. The breast pump system further comprises an attachment member which is configured to attach a second end of the tube 4 either to another part of the tube 4 or to the housing, for example so that a tube wrapped around the housing can be maintained in its wrapped position so that the breast pump system can easily be stored. Alternatively, the attachment member is configured to attach the second end of the tube to the main body 7, for example when the breast pump system is in use. The attachment member may be a clip which may be integrally formed with the main body 7 or the housing of the operating unit. An example of a clip 30 configured to attach the second end of the tube 4 to another part of the tube is shown in FIG. 10. The clip 30 comprises two pair of arms 31, 32 configured to grip around a tube.

Figure 9:
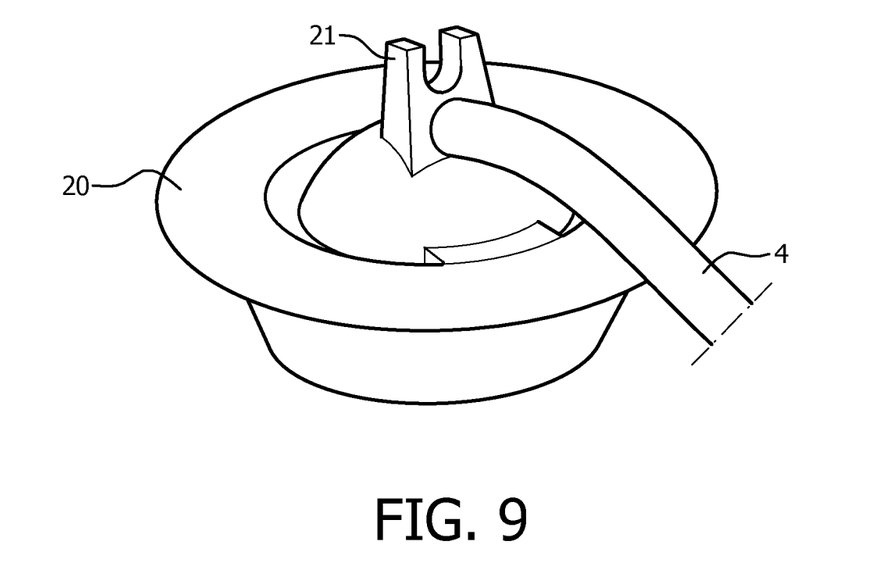
FIG. 9 shows an embodiment of an attachment member.

In another embodiment, the attachment member comprises a cap 20 as seen in FIG. 9. The cap 20 comprises an air passage which is attachable to the second end of the tube 4. The cap 20 is further configured to be removably attachable to a main body 7 of an expression unit 3 such that the cap 20 forms an upper part of the vacuum chamber of the expression unit 3 when the cap is attached to the main body 7. Thus, when the cap 20 is attached to the main body 7 and the vacuum pump is operated, air is pumped out of the vacuum chamber through the air passage of the cap 20 and into the tube 4 which causes the membrane to deform or invert. This results in an indirect vacuum being generated in the funnel 5 of the expression unit. Due to the presence of the membrane, the cap 20 and the tube 4 is not generally in contact with expressed milk and so it is unlikely that they will need to be disassembled and sterilised. The attachment member further comprises a clip 21 as seen in FIG. 9. The cap 20 can be integrally formed with the clip 21 by injection moulding.

As the first end of the tube 4 is attached to the housing and the second end of the tube 4 is attached to the cap 20, it is signalled to the user that after use they can wrap the tube 4 around the housing so that the operating unit 3 can be stored without damaging the tube 4. Furthermore, as the attachment member comprises a cap 20 and a clip, and because the attachment member is used for securing the tube in a wrapped position, the risk of accidentally losing the cap when the breast pump is stored is reduced.

In an alternative embodiment, the first end of the tube 4 is not connected to the connector 15. In this embodiment, the tube 4 is wrapped around the housing and is secured in its wrapped position by an attachment member which is configured to attach the first end of the tube with the second end of the tube. The attachment member may be a clip as illustrated in FIG. 10.

The attachment member provides the advantage that when the tube 4 is a wrapped around the housing it can be secured in its wrapped position such that the operating unit 3 and the tube 4 can easily be packed away, stored or transported. Furthermore, there are no loosely hanging parts which may otherwise be damaged. Additionally, when the tube 4 is wrapped around the housing, it is signalled to the user that it can easily be unwound and used immediately.

It is further envisaged that in an alternative un-illustrated embodiment, the operating unit is further connectable to the mains power supply via an electrical cable or connector. In this embodiment, the outer surface of the operating unit according to any of the embodiments described above can additionally or alternatively be used for wrapping the electrical cable about the housing of the operating unit. Thus, when the breast pump system 1 has been used and is dissembled to be put away, the tube 4 and/or the electrical cable can be wrapped around the outer surface of the side wall 10 of the housing.

Although the above breast pump system has been described to comprise one connector and one tube, it is envisaged that the breast pump system according to any of the embodiments described above further comprises a second connector located in a second recess and that a first end of a second tube is attachable to the connector and a second end of the second tube is attachable to a second expression unit such that a user can express milk from both breasts simultaneously.

It is to be understood that the term "buckling" with reference to the tube in the description above includes and covers collapsing, kinking or folding. Thus, the section of the outer surface that is curved enables the tube to be wrapped about the housing without buckling, collapsing, kinking or folding.

It will be appreciated that the term "comprising" does not exclude other elements or steps and that the indefinite article "a" or "an" does not exclude a plurality. A single processor may fulfil the functions of several items recited in the claims. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. An operating unit for a breast pump system comprising a housing and a vacuum pump disposed in said housing, the housing having a connector configured for attachment of a first end of a tube and an elongated outer surface region about which the tube can be wrapped;
   at least part of the elongated outer surface region being curved so as to provide a first path for guiding and supporting the tube without buckling as said tube is wrapped around the housing; and
   the connector being disposed in a recess of the housing defined, at least in part, by a curved surface region shaped so as to provide a second path for guiding and supporting the tube from the connector to the first path without buckling.

2. An operating unit according to claim 1 where at least the part of the elongated outer surface region that is curved comprises a plurality of linear sections that extend at an oblique angle to each other.

3. An operating unit according to claim 1 where at least the part of the elongated outer surface region that is curved has a radius.

4. An operating unit according to claim 1 where the elongated outer surface includes a straight section.

5. An operating unit according to claim 1 where the elongated outer surface has a lip configured to retain a tube wrapped around the housing.

6. An operating unit according to claim 1 where the elongated outer surface is formed with at least one ridge for guiding the tube around the housing.

7. An operating unit according to claim 1 where the connector comprises a hollow pin extending from the recess such that a tube can be attached to the pin by inserting the pin into the tube.

8. An operating unit according to claim 7 where the hollow pin is integrally formed with the curved surface region defining the recess.

9. A breast pump system including an operating unit comprising a housing, a vacuum pump disposed in said housing, and a tube having a first end and a second end, the housing having a connector configured for attachment to the first end of the tube and an elongated outer surface region about which the tube can be wrapped;
   at least part of the elongated outer surface region being curved so as to provide a first path for guiding and supporting the tube without buckling as said tube is wrapped around the housing;
   the connector being disposed in a recess of the housing defined, at least in part, by a curved surface region shaped so as to provide a second path for guiding and supporting the tube from the connector to the first path without buckling; and the breast pump system comprising an attachment member configured to secure the second end of tube when the tube is wrapped around the housing.

10. A breast pump system according to claim 9 where the attachment member is configured to attach the second end of the tube to another part of the tube.

11. A breast pump system according to claim 9 where the attachment member is configured to attach the second end of the tube to the housing.

12. A breast pump system according to claim 9 where the attachment member comprises a cap configured to be removably attachable to a main body of an expression unit.

13. A breast pump system according to claim 12 where the cap is configured for attachment to the second end of the tube and the cap comprises a clip configured to be removably attachable to another part of the tube.

14. A breast pump system according to claim 9 where the attachment member is configured to attach the first end of the tube with the second end of the tube when the tube is wrapped around the housing.

* * * * *